US012599775B2

(12) United States Patent
DiMino et al.

(10) Patent No.: US 12,599,775 B2
(45) Date of Patent: Apr. 14, 2026

(54) PULSED RADIO FREQUENCY THERAPY SYSTEM, APPARATUS AND METHOD FOR USING SAME

(71) Applicant: ADM Tronics Unlimited, Inc., Northvale, NJ (US)

(72) Inventors: Andre' DiMino, Woodcliff Lake, NM (US); Matthew Drummer, Fort Lee, NJ (US)

( * ) Notice: Subject to any disclaimer, the term of this patent is extended or adjusted under 35 U.S.C. 154(b) by 719 days.

(21) Appl. No.: 17/900,521

(22) Filed: Aug. 31, 2022

(65) Prior Publication Data

US 2023/0062693 A1 Mar. 2, 2023

Related U.S. Application Data

(60) Provisional application No. 63/239,292, filed on Aug. 31, 2021.

(51) Int. Cl.
*A61N 1/40* (2006.01)
*A61N 1/02* (2006.01)

(52) U.S. Cl.
CPC .............. *A61N 1/40* (2013.01); *A61N 1/025* (2013.01)

(58) Field of Classification Search
CPC ........... A61N 1/025; A61N 1/40; A61N 1/403
See application file for complete search history.

(56) References Cited

U.S. PATENT DOCUMENTS

| | | |
|---|---|---|
| 4,667,677 A | 5/1987 | DiMino |
| 5,190,037 A | 3/1993 | DiMino |
| 5,249,575 A | 10/1993 | DiMino |
| 5,676,695 A | 10/1997 | DiMino |
| 2008/0082145 A1* | 4/2008 | Skwarek ............ A61B 18/1206 607/60 |
| 2011/0144636 A1* | 6/2011 | Alexander ............. A61B 18/00 606/34 |

FOREIGN PATENT DOCUMENTS

WO WO-2016032666 A1 * 3/2016 ............. A61B 90/90

* cited by examiner

*Primary Examiner* — Kaitlyn E Smith
(74) *Attorney, Agent, or Firm* — Len Taylor Patent Attorney; Leonard B. Taylor

(57) ABSTRACT

The present invention relates to a pulsed radio frequency therapy system adapted to project the beam onto the skin surface of a living body overlying a problem region, the beam serving to relieve pain and to obtain other health related beneficial effects. The system includes an energy-generating unit in which a radio-frequency carrier is over-modulated by a sonic signal to produce periodic bursts of radio-frequency energy whose repetition rate corresponds to the frequency of the signal. The output of the unit is fed to a tank circuit tuned to the carrier frequency and housed within the barrel of a portable applicator gun. Supported within the barrel and coupled to the tank circuit is a discharge electrode whose tip is adjacent to the mouth of the barrel whereby a pulsed radio frequency is projected from the tip. The portable applicator gun includes automated applicator coil tuning, automated coil protection, and a phase-up conditioning system. The energy generating unit includes a lifespan sensing system which includes a modem, a GPS, and a transceiver so that the pulsed radio frequency therapy system may transfer and/or receive information wirelessly to an external storage and/or processing area which tracks the usage, wear and tear, location, and other treatment data of the user and the therapy system.

9 Claims, 11 Drawing Sheets

PULSED RADIO FREQUENCY THERAPY SYSTEM, APPARATUS AND METHOD FOR USING SAME

CROSS REFERENCE TO RELATED APPLICATIONS

This patent application claims the benefit of U.S. Patent Provisional Application No. 63/239,292, filed on Aug. 31, 2021, which is incorporated herein by reference in its entirety.

BACKGROUND OF THE INVENTION

Field of the Invention

The present disclosure relates to a pulsed radio frequency therapy system in which the output of a unit producing periodic bursts of radio-frequency energy is applied to a tank circuit connected to a discharge electrode from whose tip a pulsed radio frequency is projected onto the skin surface of a living body being treated, and more particularly to an applicator which is self-adjusting, and collects usage and setting information for a user.

Description of the Related Arts

Conventional pulsed radio frequency therapy treatment systems on the market have many shortcomings as the conventional systems include applicators which are manually adjusted, applicator coils which can burn out due to a user inadvertently placing their hand or other body part in dose proximity to the applicator coils, and a sudden loud tone caused by a 1 KHz modulation frequency of the output signal from the applicator.

SUMMARY OF THE INVENTION

Embodiments of the present disclosure have been provided to address the shortcomings of conventional pulsed radio frequency therapy technology and relate to an applicator which is both effective for serving to relieve pain and to produce other salutary effects, and able to gather information and statistics pertaining to a user's treatment.

In an embodiment of the present disclosure, the applicator of the present invention includes automated applicator coil tuning. The phase of the drive carrier frequency is compared with the phase received from a small pickup antenna located in close proximity to the secondary winding of the applicator coil to adjust the carrier drive carrier frequency to the resonant frequency of the secondary coil.

In an embodiment of the present disclosure, the applicator includes automatic applicator coil protection. That is, the resonant frequency from the Automated Applicator Coil Tuning is monitored. If the resonant frequency deviates outside of a threshold range, as would happen if the user accidently places their hand in dose proximity to the applicator coil, the drive to the applicator coils is terminated.

In an embodiment of the present disclosure, the applicator includes a conditioning system for gradual phase-up of pulsed radio frequency output. For example, to avoid startling an animal or human with a sudden loud tone caused by a 1 KHz modulation frequency of the output signal, the current to the output applicator is controlled. The current to the output is initially set low and is gradually ramped up resulting in an initial smaller pulsed radio frequency with a lower volume that gradually ramps up to full power and volume.

In an embodiment of the present disclosure, the applicator includes a sensing system for signifying replacement prior to efficacy reduction. The user replaceable applicator assembly contains memory elements that interface with the main system control. The memory elements contain data that uniquely identifies each applicator. The main system controller can write data to the memory elements in the applicator assembly in order to track the amount of time the applicator is actively delivering treatments. Using this usage data time, the system controller is able to monitor and limit the maximum lifespan of an applicator assembly. Data can be communicated to the cloud for remote monitoring and reporting.

The above and yet other objects and advantages of the present disclosure will become apparent from the hereinafter set forth Brief Description of the Drawings and Detailed Description of the Invention.

It is intended that any other advantages and objects of the present disclosure that become apparent from the detailed description, drawings or illustrations contained herein are within the scope of the present disclosure. It is also intended that any feature and limitation listed in an embodiment of the present disclosure can be used in any other embodiment of the present disclosure unless specifically stated otherwise.

BRIEF DESCRIPTION OF THE DRAWINGS

The above and other objects and features of the present disclosure will become better understood with regard to the following description of the embodiments given in conjunction with the accompanying drawings, in which.

It is intended that any other embodiments of the present disclosure that result from any changes in application or method of use or operation, method of manufacture, shape, size or material which are not specified within the detailed written description or illustrations and drawings contained herein, yet are considered apparent to one skilled in the art, are within the scope of the present disclosure. Furthermore, various features of the embodiments disclosed may be combined with each other to form additional embodiments.

DETAILED DESCRIPTION OF THE INVENTION

Hereinafter, various embodiments of the present disclosure will be described in detail along with the accompanying drawings.

Figure 1:
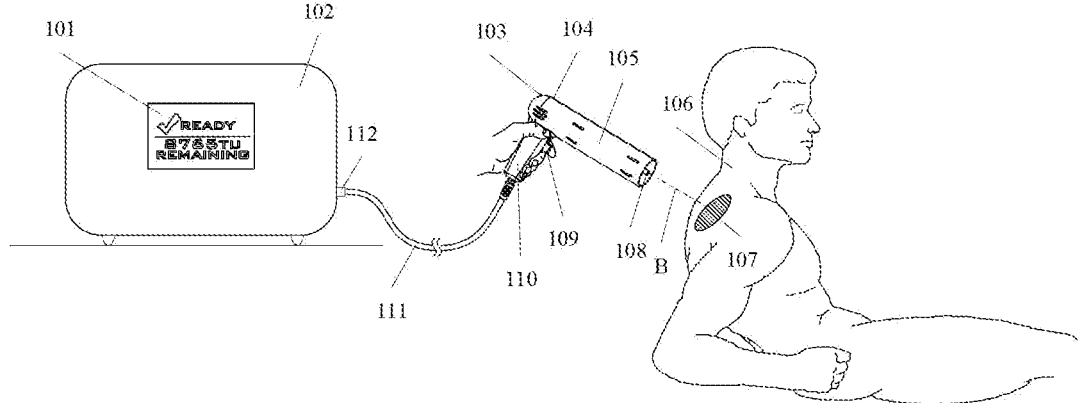
FIG. 1 illustrates a pulsed radio frequency therapy system in accordance with an embodiment of the present disclosure.

FIG. 1 illustrates a pulsed radio frequency therapy system in accordance with an embodiment of the present disclosure.

A pulsed radio frequency therapy system includes an energy-generating unit 102 which yields periodic bursts of radio-frequency energy whose repetition rate is at a sonic frequency. This energy is applied via a relatively long, flexible cable 111 connected to a hand-held portable applicator 104 within whose barrel 105 is mounted a discharge electrode 108 from which is projected a pulsed radio frequency beam B. Beam B is directed toward the skin surface 106 of a user that overlies a problem region 107 in the body of a user. The energy-generating unit 102 may also include a mufti-function display panel 101 which displays a variety of information such as, for example, a "READY" status for the energy generating unit 102 and number of treatments remaining for a particular applicator 104. The other end of the flexible cable 111 is connected to the energy generating unit via an output jack 112. Settings for the energy-generating unit can be viewed using the multi-function display panel 101 which may display text and graphics. In an embodiment the settings may include low, medium, and high power, as well as other settings, for example, treatment time used. Furthermore, the settings may include more or fewer power alternatives, for example, a single power setting, two power settings, or 3 or more power settings. The multi-function display panel 101 may be a Liquid Crystal Display (LCD) or a Light Emitting Diode (LED). However, other types of readouts which can display text and graphics can be used, for example, a touch sensitive display.

During operation, a user turns a key (not shown) on the energy generating unit then presses a button (not shown) to place the unit in ready-standby mode. However, other conventional methods of turning on an energy generating unit can be used, for example, a button, a switch, a key, or any combination thereof. When the unit is in ready-standby mode, an applicator indicator 103 on the applicator 104 illuminates, which notifies the user that the applicator is ready to use. Additionally, the applicator indicator 103 may include a beep or any combination of a light and an audible signal. Once the unit is in ready-standby mode, treatment is activated by a user pressing a trigger activation switch 109 on an applicator grip 110.

A configuration of the energy-generating unit and various processes which it uses to generate periodic bursts of radio-frequency energy are disclosed in U.S. Pat. No. 4,667,677 to DiMino ("DiMino'677"), U.S. Pat. No. 5,190,037 to DiMino et al. ("DiMino'037"), U.S. Pat. No. 5,249,575 to DiMino et al. ("DiMino'575"), and U.S. Pat. No. 5,676,695 to DiMino et al. ("DiMino'695"), all of the disclosures of which are herein incorporated by reference in their entirety.

Furthermore, the various electrical components which configure the energy-generating units as disclosed in DiMino'677, DiMino'037, DiMino'575, and DiMino'695 may be replaced with state of the art, equivalent solid state electronic components, such as transistors, semiconductors, and the like.

Figure 2:
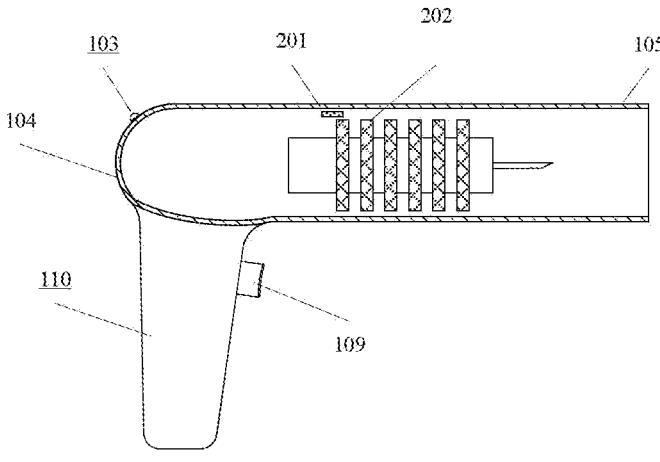
FIG. 2 is a side view illustrating a pulsed radio frequency therapy applicator having automated applicator coil tuning in accordance with an embodiment of the present disclosure.

FIG. 2 is a side view illustrating a pulsed radio frequency therapy applicator having automated coil tuning in accordance with an embodiment of the present disclosure As shown in figure FIG. 2, the pulsed radio frequency therapy applicator 104 ("applicator") can be configured to be hand-held and portable, however, other configurations may be used, for example, a stationary floor mounted applicator. The applicator 104 may be constructed in the form of a gun having an applicator grip 110 and a trigger activation switch 109 mounted thereon. The trigger activation switch 109, one contact of which is grounded, is connected by a flexible cable 111 to energy generating unit 102. In this way, the applicator 104 is only activated when an operator holding the applicator 104 in his hand actuates the trigger activation switch 109. A user can determine that the applicator is ready for treatment by viewing the applicator indicator 103. In practice, the trigger activation switch may be arranged to actuate a relay having a time delay characteristic, so that once the trigger 109 is momentarily pulled, the applicator 104 is turned on for a set period of treatment time, for example, a 15-second interval, and does not turn off until the interval is completed. Once the interval is completed, the applicator 104 enters a rest state for a set period of time, for example a 3 second interval. During the rest state the applicator 104 may not be activated by pressing the trigger activation switch 109. After the rest state is completed, the user may once again apply treatment by pressing the trigger activation switch 109 and the applicator 104 is once again turned on for the set period of treatment time.

Additionally, the applicator 104 includes automated applicator coil tuning. In an embodiment, a feedback pickup antenna 201 and tank coil 202 having secondary winding are included in the applicator 104 which advantageously allows the phase of the drive carrier frequency to be compared with the phase received from the pickup antenna 201 which is positioned in dose proximity to the tank coil 202 of an applicator in order to adjust the carrier drive frequency to the resonant frequency of the tank coil 202. The tank coil 202 may be an interchangeable component of the applicator 104 thereby advantageously permitting a user to replace the tank coil 202 when the secondary winding has reached the end of its useful life cycle.

Figure 3:
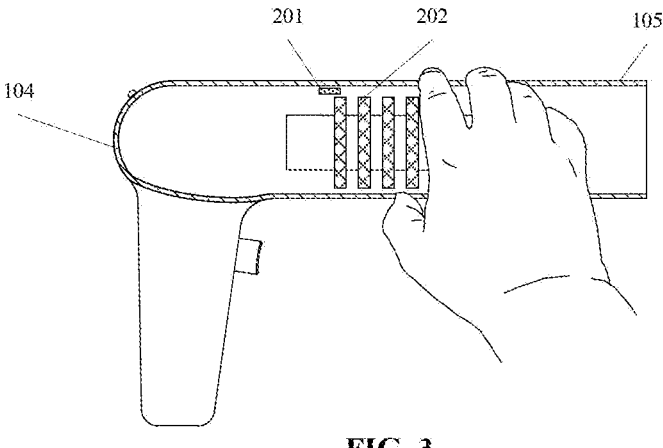
FIG. 3 is a side view illustrating a pulsed radio frequency therapy applicator having automated coil protection in accordance with an embodiment of the present disclosure.

FIG. 3 is a side view illustrating a pulsed radio frequency therapy applicator having automated coil protection in accordance with an embodiment of the present disclosure.

As described above, the applicator 104 includes a pickup antenna 201 which is positioned in close proximity to the tank coil 202 of an applicator coil to adjust the carrier drive frequency to the resonant frequency of the tank coil 202. The pickup antenna 201 picks up a signal from the tank coil 202 and compares it with a sending signal from the energy generating unit 102. When the signal comparison is out of phase by a threshold number of degrees, for example, less than or greater than 90 degrees the applicator 104 shuts off, however other thresholds may be used. This allows the resonant frequency of the automated applicator coil tuning to be monitored which advantageously terminates the drive to the applicator 104 when the resonant frequency deviates outside of a threshold range, which would happen if, for example, a user accidentally places their hand in dose proximity to the applicator gun barrel 105 housing the tank coil 202.

Figure 4:
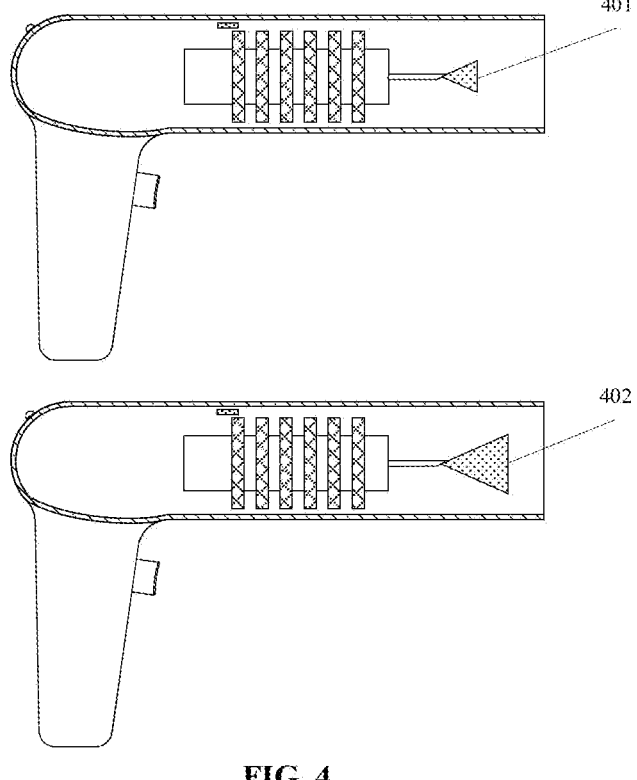
FIG. 4 is a side view illustrating a pulsed radio frequency therapy applicator having a phase-up conditioning system in accordance with an embodiment of the present disclosure.

FIG. 4 is a side view illustrating a pulsed radio frequency therapy applicator with a phase-up conditioning system in accordance with an embodiment of the present disclosure.

In an embodiment, the pulsed radio frequency therapy system may also be used to treat animals. Since an operator of the system is free to manipulate the applicator 104 which is connected to energy generating unit 102 by a long cable 111 (for example, 6 feet in length, however, other lengths may be used), the operator is able to treat any region of a human or animal. In treating an animal such as a horse, the audio sound produced by conventional pulsed radio frequency therapy systems when a pulsed radio frequency discharge takes place may startle the animal and make it difficult to treat the animal. To avoid startling an animal with a sudden loud tone caused by a 1 KHz modulation frequency of the output signal, the current to the applicator 104 is advantageously controlled by initially setting the current to the output signal low then gradually ramping up the current which results in an initial smaller pulsed radio frequency corona 401 with a lower volume that gradually ramps up to full power and volume to generate a larger pulsed radio frequency corona 402. In an embodiment the power settings may include low, medium, and high power, as well as other settings for example, treatment time used. The power settings may be controlled by a switch (not shown) which adjusts the power to low, medium, or high, however the number of power settings may vary from a single power setting to more than 3 power settings. On low power, a reduced pulsed radio frequency corona beam exits the applicator 104 and on high power, a pulsed radio frequency beam greater than the reduced beam 401 exits the applicator 104.

Figure 5:
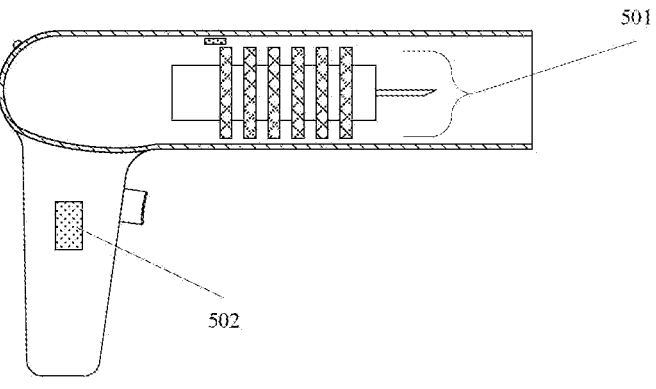
FIG. 5 is a side view illustrating a pulsed radio frequency therapy applicator having a lifespan sensing system in accordance with an embodiment of the present disclosure.

FIG. 5 is a side view illustrating a pulsed radio frequency therapy applicator having a lifespan sensing system in accordance with an embodiment of the present disclosure.

In conventional pulsed radio frequency therapy systems, an applicator experiences reduced efficacy due to repeated usage over a period of time. However, in an embodiment of the present disclosure, the applicator 104 includes an internal assembly 501 which can be replaced by a user. The energy generating unit 102 may include a modem, a GPS, and a transceiver so that data for the applicator 104 may be transferred and/or received wirelessly to an external storage and/or processing area, such as a smart phone, a cell phone, the cloud, and the internet. However, the modem, the GPS, and the transceiver can also be disposed in the applicator 104 or in a combination of the energy generating unit 102 and the applicator 104. To determine when the applicator 104 needs to be replaced, the applicator 104 includes a sensing system with memory elements 502 which tracks an amount of time that the applicator 104 has been actively delivering treatments. The internal assembly 501 includes memory elements 502 that interface with the main system controller of the generating unit. However, the memory elements 502 can be included in the energy generating unit 102, the applicator 104, or in a combination of the applicator 104 and the energy generating unit 102. The memory elements capture data from the applicator, such as, data which uniquely identifies each applicator, the number of uses of the applicator, the amount of time the applicator has been used per application, and a total amount of time that the applicator has been used. The main system controller can be disposed in the energy-generating unit 102, the applicator 104, or a combination of both. The main system controller writes usage data to the memory elements 502 which track the amount of time, energy settings, and other information when the applicator 104 is actively delivering treatments. Using the usage data, the main system controller is able to monitor and limit the maximum lifespan of the internal assembly 501. Additionally, data can be communicated to the cloud for remote monitoring and reporting, via a wired connection, a wireless connection, or a combination of both.

Figure 6:
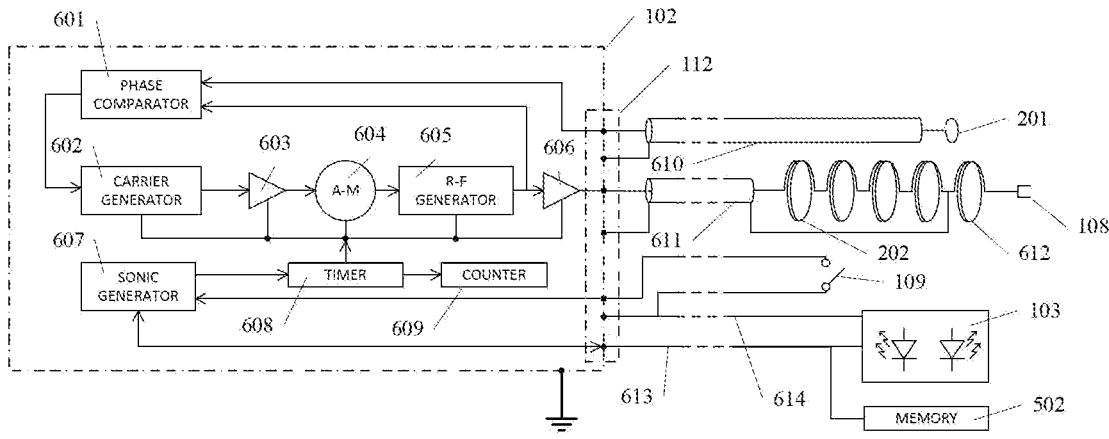
FIG. 6 illustrates an internal configuration of an energy generating unit and an internal configuration of a pulsed radio frequency therapy applicator in accordance with an embodiment of the present disclosure.

FIG. 6 illustrates an internal configuration of an energy generating unit and an internal configuration of a pulsed radio frequency therapy applicator in accordance with an embodiment of the present disclosure.

Referring to FIG. 6, an energy generating unit 102 in accordance with embodiment of the present disclosure includes a phase comparator 601, a RF carrier generator 602, an audio amplifier 603, an amplitude modulator 604, a R-F generator 605, an output amplifier 606, an audio frequency range generator 607, a cycle timer 608, and a counter timer 609. Information and/or signals are sent to the applicator 104 via an output jack 112 of the energy generating unit. The pulsed radio frequency therapy applicator includes an electrode tip 108, a trigger switch 109, a flexible coax cable 610 for input from feedback pickup antenna 201, a flexible coax cable 611 for output to 202 tank coil, an output coil 612 that is inductively coupled to 202 tank coil, a serial data cable 613 which sends signals to control a memory 502 and applicator status indicator lights 103, and a low voltage power line 614.

The phase of the output RF signal from the RF generator 605 is compared with the signal from the feedback pickup antenna 201. The output of the phase comparator is sent to the carrier generator 602. For optimal tuning the phase of the RF generator 605 and the phase of the signal received from the feedback pickup antenna 201 should be the same. If the carrier frequency is lower or higher than optimal, the phase from the feedback pickup antenna 201 will either lag or lead the RF generator 605 waveform. The carrier generator 602 will adjust the carrier frequency until the phase difference is null.

The carrier generator 602 monitors the phase once optimal tuning has been achieved (zero phase difference). If the phase deviates more than a set threshold once tuned, the carrier generator will terminate thus stopping the treatment.

This would happen if the output coil 612 is loaded by a user placing their hand or other conductive material in proximity to the barrel of the applicator gun 105 as shown in FIG. 3.

Figure 7:
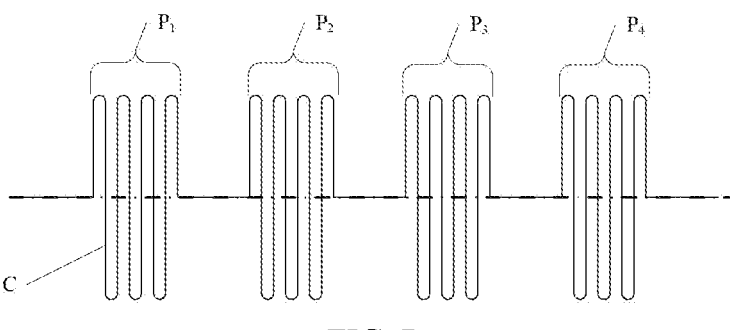
FIG. 7 illustrates bursts of radio frequency energy in accordance with an embodiment of the present disclosure.

FIG. 7 illustrates bursts of radio frequency energy in accordance with an embodiment of the present disclosure.

Referring to FIG. 7, $P_1$ thru $P_4$ are bursts of radio frequency energy. Radio frequency carrier C is overmodulated by a sonic frequency signal, thereby giving rise to the periodic bursts $P_1$, $P_2$, $P_3$, etc.

Figure 8:
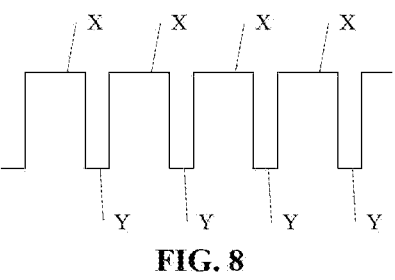
FIG. 8 illustrates pulse durations of an on/off waveform in accordance with an embodiment of the present disclosure.

FIG. 8 illustrates pulse durations of an on/off waveform in accordance with an embodiment of the present disclosure.

Referring to FIG. 8, an example of cycle X which may have an "on" duration of 15 seconds and a relaxation interval Y which may have an "off" duration of 3 seconds is illustrated. However, other "on" durations and "off" durations may be used.

Figure 9:
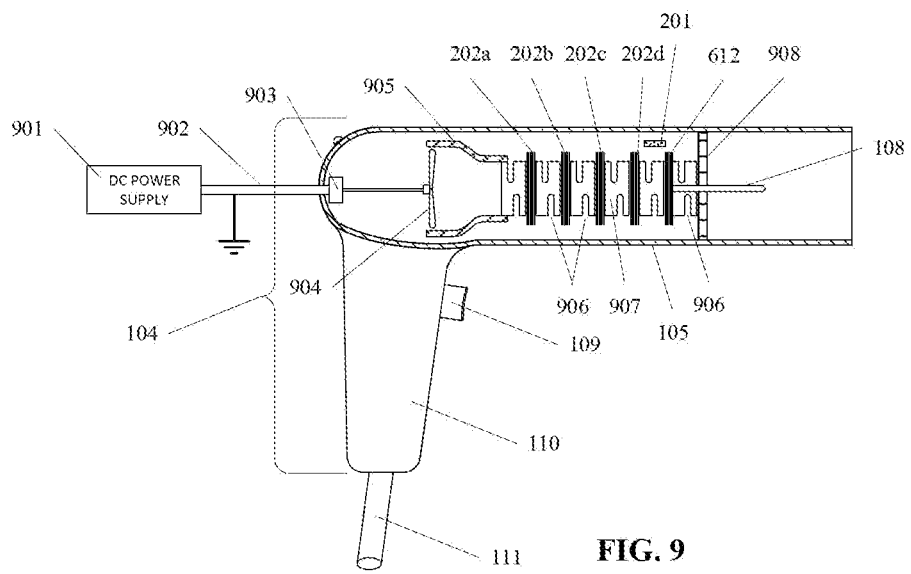
FIG. 9 illustrates a pulsed radio frequency therapy applicator in accordance with an embodiment of the present disclosure.

FIG. 9 illustrates a pulsed radio frequency therapy applicator in accordance with an embodiment of the present disclosure.

In FIG. 9, a side view of an applicator 104 in accordance with an embodiment of the present disclosure includes a dc power supply 901, a line 902 connecting the dc power supply to a motor-driven 903 ventilator fan 904 supported on an inner wall of an aperture plate coupled to a shroud 905 which directs air flow from an opening in the tube through a hollow tank coil core 907 in the applicator gun barrel 105 so that air drawn from the atmosphere is blown into the applicator gun barrel 105. An insulating wafer 908 is positioned next to the tank coil 907. The air is discharged from slots 906 to prevent overheating of the tank circuit and to maintain the efficiency of the unit even after prolonged operation.

The applicator 104 further includes an electrode tip 108, a trigger switch 109, a hand grip 110, a flexible multi coax/conductor cable 111 which includes cables 610, 611, 613 and 614 shown in FIG. 6, a feedback pickup antenna 201, a tank coil divided into equal spaced pie sections 202*a-d*, and an output coil 612 that is inductively coupled to tank coil 202.

Figure 10:
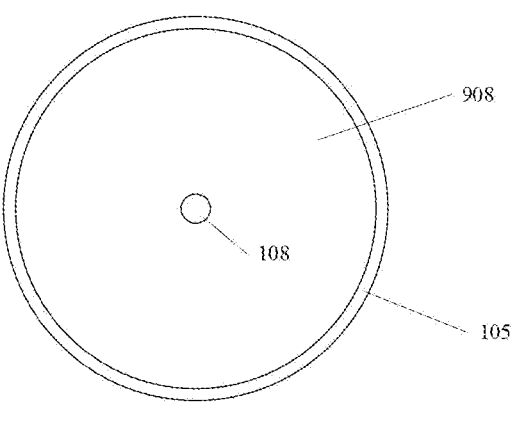
FIG. 10 illustrates a front view of a pulsed radio frequency therapy applicator in accordance with an embodiment of the present disclosure.

FIG. 10 illustrates a front view of a mouth of a pulsed radio frequency therapy applicator in accordance with an embodiment of the present disclosure.

Referring to FIG. 10, a front view of the applicator barrel 105, a discharge electrode 614, and a circular insulating wafer 908 are illustrated.

Figure 11:
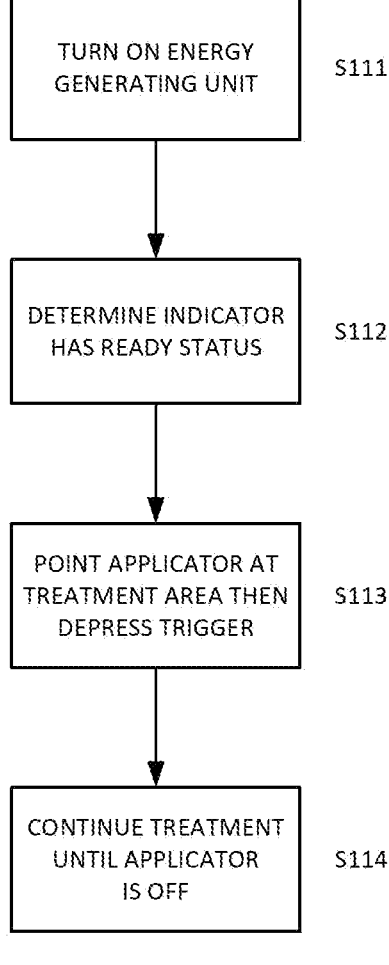
FIG. 11 illustrates a method of using a pulsed radio frequency therapy system in accordance with an embodiment of the present disclosure.

FIG. 11 illustrates a method of using a pulsed radio frequency therapy system in accordance with an embodiment of the present disclosure.

Referring to FIG. 11, turning an energy generating unit on in order to supply power to the energy generating unit (S111), determining that an indicator on the energy generating unit has a Ready status (S112), in response to the determination that the applicator has a Ready status, pointing the applicator at a desired treatment area then depressing a trigger on the applicator connected to the energy generating unit to deliver treatment (S113), and continuing treatment until the applicator has turned off (S114).

While the present invention has been described with respect to certain embodiments, it will be apparent to those skilled in the art that various changes and modifications may be made without departing from the scope and spirit of the invention. Furthermore, the embodiments may be combined to for additional embodiments.

What is claimed is:

1. A pulsed radio frequency therapy system comprising:
   an energy generator including a phase comparator, a carrier generator, and a RF generator;
   an applicator including a feedback pickup antenna, the applicator connected to the energy generator;
   wherein the phase comparator compares a phase of an output RF signal from the RF generator with a phase of a signal from the feedback pickup antenna then sends the comparison results to the carrier generator,
   wherein when the phase of the output RF signal and the phase of the signal from the feedback pickup antenna are not the same the carrier generator adjusts a carrier frequency until a phase difference is null,
   wherein when the phase difference is null, the carrier generator continues to monitor the phase difference so that the phase difference does not exceed a set threshold amount, and
   wherein when the phase difference exceeds the set threshold amount the carrier generator terminates operation to stop treatment.

2. The pulsed radio frequency therapy system of claim 1, wherein the applicator further includes a first internal assembly having a first sensing system,
   wherein the first sensing system is configured to record usage data of the first internal assembly and store the usage data in memory, and wherein when the usage data of the first internal assembly exceeds a threshold usage amount replacing the first internal assembly with a second internal assembly having a second sensing system.

3. The pulsed radio frequency therapy system of claim 2, wherein the usage data includes an applicator id, a number of uses of the applicator, an amount of time per usage, a total amount of usage time or any combination thereof.

4. The pulsed radio frequency therapy system of claim 2, wherein the memory is included in the energy generator.

5. The pulsed radio frequency system of claim 2, wherein the memory is included in the applicator.

6. The pulsed radio frequency system of claim 2, wherein the memory is included in a wireless device which communicates with the energy generator.

7. The pulsed radio frequency system of claim 2, wherein the memory is included in a wireless device which communicates with the applicator.

8. A method of using a pulsed radio frequency therapy system including an energy generator having a phase comparator, a carrier generator, and a RF generator, connected to an applicator having a feedback pickup antenna, the method comprising:
   comparing by the phase comparator a phase of an output RF signal from the RF generator with a phase of a signal from the feedback pickup antenna and sending the comparison results to the carrier generator,
   adjusting a carrier frequency by the carrier generator when the phase of the output RF signal and the phase of the signal from the feedback pickup antenna are not the same, until a phase difference is null,
   continuously monitoring the phase difference by the carrier generator when the difference is null, so that the phase difference does not exceed a set threshold amount, and
   terminating operation of the carrier generator to stop treatment when the phase difference exceeds the set threshold amount.

9. A method of using a pulsed radio frequency therapy system including an energy generator connected to an applicator having an internal assembly, a sensing system, and a timer, the method comprising:
   turning the energy generator on to supply power to the applicator;
   determining whether the internal assembly of the applicator needs to be replaced by viewing usage data captured by the sensing system and stored in a memory;
   in response to a determination that the internal assembly needs to be replaced replacing the internal assembly with another internal assembly;
   setting the timer to a set threshold
   pointing the applicator at a desired treatment area then depressing a trigger on the applicator to deliver treatment; and
   continuing treatment until the timer has exceeded the set threshold,
   wherein the usage data stored in the memory is reset when the internal assembly is replaced, and
   wherein current to the applicator is controlled by setting the current to a low output signal then gradually ramping up the current to a higher output signal.

* * * * *